United States Patent
Hong et al.

(10) Patent No.: US 9,075,054 B2
(45) Date of Patent: Jul. 7, 2015

(54) C-REACTIVE PROTEIN IMPRINTED POLYMER FILM AND MICROCHIP SYSTEM UTILIZING THE SAME

(71) Applicants: Mackay Memorial Hospital, Taipei (TW); National Tsing Hua University, Hsinchu (TW)

(72) Inventors: Chien-Chong Hong, Hsinchu (TW); Szu-Ying Chen, Hsinchu (TW); Jia-Cherng Horng, Hsinchu (TV); Chie-Pein Chen, Taipei (TW)

(73) Assignees: MACKAY MEMORIAL HOSPITAL, Taipei (TW); NATIONAL TSING HUA UNIVERSITY, Hsinchu (TW)

( * ) Notice: Subject to any disclaimer, the term of this patent is extended or adjusted under 35 U.S.C. 154(b) by 425 days.

(21) Appl. No.: 13/715,693

(22) Filed: Dec. 14, 2012

(65) Prior Publication Data
US 2013/0156645 A1    Jun. 20, 2013

(30) Foreign Application Priority Data
Dec. 16, 2011    (TW) .............................. 100146860 A

(51) Int. Cl.
| | |
|---|---|
| *G01N 15/06* | (2006.01) |
| *G01N 33/00* | (2006.01) |
| *G01N 33/48* | (2006.01) |
| *G01N 33/545* | (2006.01) |

(52) U.S. Cl.
CPC ....... *G01N 33/545* (2013.01); *Y10T 428/24479* (2015.01); *G01N 2333/4737* (2013.01)

(58) Field of Classification Search
USPC ............... 422/50, 68.1, 502, 503, 504, 82.01, 422/82.02; 436/43
See application file for complete search history.

(56) References Cited

U.S. PATENT DOCUMENTS

2004/0186359 A1*    9/2004    Beaudoin et al. ............. 600/310

OTHER PUBLICATIONS

Wen Chung et al., "Point-of-Care C-Reactive Protein Testing Based on High-Specific and Long-Shelf-Life Plastic Antibody Films", ISMM 2012, The 4th international Symposium on Microchemistry and Microsystems, Jun. 10-13, 2012, Sheraton Hsinchu Hotel, Hsinchu, Taiwan.
Chien-Chong Hong et al., "Electronic Microfluidic Biochips With Immune-Like Biosensors for Rapid Detection of C-Reactive Protein in Human Serum", 16th International Conference on Miniaturized Systems for Chemistry and Life Sciences, Oct. 28-Nov. 1, 2012, Okinawa, Japan.

* cited by examiner

*Primary Examiner* — Brian J Sines
(74) *Attorney, Agent, or Firm* — WPAT, P.C.; Anthony King

(57) ABSTRACT

The present invention is a C-reactive protein imprinted polymer film. The C-reactive protein antibody imprinted polymer film comprises a plurality of imprinted nanocavities with unified orientation and distribution formed by removing a plurality of C-reactive proteins from a polymer film. Its ability to capture the target proteins can achieve 99% compared with the natural antibodies. The present invention further provides a C-reactive protein microchip system formed by the dynamic capacitance sensing method with the above imprinted polymer film. The C-reactive protein microchip system comprises a body having a first chamber and a second chamber, and a detector.

20 Claims, 13 Drawing Sheets

C-REACTIVE PROTEIN IMPRINTED POLYMER FILM AND MICROCHIP SYSTEM UTILIZING THE SAME

CROSS-REFERENCES TO RELATED APPLICATIONS

This application claims priority to Taiwan Patent Application No. 100146860 filed on 16 Dec. 2011. All disclosure of which is incorporated herein by reference in its entirety.

BACKGROUND OF THE INVENTION

1. Field of the Invention

The present invention relates to a protein imprinted polymer film, especially a C-reactive protein imprinted polymer film and microchip system using the same.

2. Description of the Related Art

Nowadays medical technology has reached a certain level, but still faces disease with low cure rate and is hard to diagnose. These diseases are often caused by multiple factors, and therefore hard to diagnose. Inflammation is a symptom that associates with multiple diseases, such as: infection, diabetes, cardiovascular diseases, Alzheimer's disease, allergies, cancer and autoimmune diseases. This discovery appeared on the cover of Time magazine in 2004.

The characteristics that are common in these diseases caused by inflammation mainly result from multiple factors, which may make definite diagnosis very difficult, and hinder early treatment. Thus, it can even turn into an incurable and deadly disease. This makes early diagnosis very important, the sooner we can accurately diagnose the disease, the less threatening it becomes.

C-reactive protein (CRP) is secreted by the liver. The level of C-reactive protein rises up to 1,000 times higher than normal level when there is inflammation caused by trauma, ischemia, burns and infection in the body. The C-reactive protein acts as an indicator of inflammation. In clinical practices, because of its ability of detecting inflammation, it is used for screening and monitoring of organ injuries, or assesses the effectiveness of anti-inflammatory drug treatment on patients. In addition, a great proportion of premature birth is also considered as inflammation due to infection, and therefore C-reactive protein is also an important test item during pregnancy.

The risks of mortality and morbidity are higher in premature infants (delivered before 37 weeks of gestation), and prematurity is one of the greatest unsolved problems in perinatology. Preterm birth is a disease that can be caused by multiple factors, thus early diagnosis can not be done easily by examining clinical symptoms or by a single exam. Therefore the development of clinical tools for early diagnosis of preterm birth is important and necessary. Since a great proportion of preterm births are due to infection with inflammation, thus elevated C-reactive protein level in a pregnant woman may indicate a possible preterm birth. When a high C-reactive protein is monitored, early preparations can be made to reduce the risks and complications of preterm birth.

Protein sensing has always been an important area in biomedical research, but nowadays most protein sensors use biological molecules as the sensing layer. An issue has been proposed in the 2010 μTAS conference, because the use of biological molecules sensing layers, this kind of exam can never be put into practice. Thus protein detecting techniques has always remained as a laboratory exam, needing a long time period to run out the results, an expert to operate the exam, and expensive laboratory instruments and chemical agents.

A molecular imprinted technology (MIT) for selectively adsorbing target molecules using target molecules imprinted in a substrate consisted of an organic polymer and an inorganic network material to form the imprinted nanocavities on the surface of the substrate. In other words, this technology can be used to make sensing layers that act similar to artificial antibodies, only it can be fabricated faster, made easier and build cheaper. The technique used to imprinting templates of small molecules has been around for decades. However, many problems are occurred when trying to imprint large protein molecules such as 1. proteins are made of multiple functional groups, making it almost impossible to get specific adsorptions; 2. proteins are giant molecules (molecular weight from 6,000 Da to several millions of Da), which are hard to be captured by imprinted nanocavities; 3. proteins are hardly dissolved in imprinted solvents; 4. the proteins are easily deformed in a stimulating environment by denaturation. Therefore, the above problems reflect the difficulty of the development of the macromolecular imprinted film.

SUMMARY OF THE INVENTION

In order to solve above problems, the present invention improves the imprinting substrate of micro-contact imprinting method different from a biomolecular film. The present invention provides a C-reactive protein imprinted polymer film, comprising a plurality of imprinted nanocavities with unified orientation and distribution formed by removing a plurality of C-reactive proteins from a polymer film, wherein the C-reactive proteins are bound to a plurality of antibodies on a modified surface of a first substrate, and wherein the modified surface of the first substrate is formed by a gold layer on the first substrate surface binding with cysteamine and glutaraldehyde in order. In another embodiment, the plurality of imprinted nanocavities with unified orientation and distribution can be easily formed by removing a plurality of C-reactive protein antibodies from a polymer film.

In one preferred embodiment of the invention, each antibody of the plurality of antibodies binds to an aldehyde group of the glutaraldehyde, which antibody does not bind to the glutaraldehyde when the aldehyde group is bound to glycine. The C-reactive proteins are connected to O-4-nitrophenylphosphoryl choline to form a plurality of precomposites, which each precomposite micro-contacts with a composition on a second substrate, and the composition is consisted of a cross-linker and an initiator with the molar ratio of the cross-linker to the initiator from 600:1 to 640:1. The cross-linker is dimethacrylate, polyethylene glycol diacrylate or trimethylolpropane triacrylate; and the initiator is 2,2'-dimethoxy-2-phenyl acetophenone, 1-hydroxy-cyclohexyl-phenyl ketone, p-phenyl benzophenone or benzyl dimethyl ketal.

The present invention also provides a C-reactive protein microchip system comprising a body having a first chamber and a second chamber, and a detector. A C-reactive protein imprinted polymer film having a plurality of imprinted nanocavities is disposed in the first chamber, and the first chamber is connected to a first portal and a second portal respectively, when a sample comprising C-reactive proteins is injected into the first portal and flowing through the C-reactive protein imprinted polymer film, flowing out of the first chamber from the second portal. A sensing electrode is disposed in the second chamber, and the second chamber is connected to a third portal and a fourth portal respectively, when an extracting solvent is injected into the first portal to extract the C-reactive proteins being captured by the imprinted nanocavities, flowing into the second chamber via the third portal, flowing out of the second chamber from the fourth portal. A detector for detecting a potential change of the sensing electrode and generating a detecting result is based on the detected potential change.

In one embodiment of the present invention, the sensing electrode is a finger electrode, and formed by a gold-plated glass material processing photolithograph. The sensing electrode has a vulcanized surface or an antibody modified surface. The potential change is base on a dynamic balancing relationship between potential energy of an equivalent circuit, formed with the sensing electrode and the extracting solution in the second chamber, and a potential energy of a sensing circuit of the detector. The detecting result is determined by a time coefficient of the potential change.

The purpose of the present invention is for the integration of protein imprinted polymer films and microfluidic chip to develop microfluidics lab-on-a-chips, replacing the traditional large-scale apparatus. The novel low-cost C-reactive protein microchip system disclosed by this invention has many advantages of compact size, high sensitivity, low cost, and fast response.

Clinical monitoring inflammation for a variety of reasons (such as preterm birth due to infection or infectious diseases), by means of detection of C-reactive protein concentration was informed that, while the addition to the traditional mass spectrometers and other large equipment for protein sensing, inspection and laboratory protein sensing the way the mainstream for an enzyme immunoassay (ELISA), but these methods must stay in the laboratory testing, and the time required for a few days, difficult to readily apparent from the patients, so the development of specialized and small of biomedical diagnostic platform has become the trend these days. The present invention is a portable clinical diagnostic tool to facilitate the diagnosis, on the one hand to control the patient's physical condition, on the one hand, to help doctors adjust the diagnostic methods and cheaper than the existing large-scale instruments quickly, closer to the needs of patients and physicians. The present invention combined micro-electromechanical chip technology with the micro fluidic chip and molecular imprinted roofs, sensor indicator protein for different causes, and hope to develop nano-biomedical sensor platform, as long as the use of trace (µL) of plasma samples that can be a variety of indicators of protein analysis, and does not require the operation of professionals. Using this analysis method will be more efficiently used to predict the possibility of the occurrence of disease.

Therefore, the present invention provides a protein imprinted polymer film by using molecular imprinted technique, which exhibit good physical stability (heat resistant) and chemical stability (anti-acid, anti-alkaline), long life cycle (several years), reusable and low-cost and other advantages are different from the bio-molecular sensing layer known in the prior art.

The present invention is further explained in the following embodiment illustration and examples. Those examples below should not, however, be considered to limit the scope of the invention, it is contemplated that modifications will readily occur to those skilled in the art, which modifications will be within the spirit of the invention and the scope of the appended claims

DETAILED DESCRIPTION OF THE INVENTION

The term "artificial antibodies" herein refers to an artificial object that can bind to a specified antigen such as the C-reactive protein imprinted polymer film of the present invention.

The term "template" or "wafer" herein means substrate.

As used herein, when a specific definition is not provided, the term "fixed orientation" herein means unified orientation.

As used herein, when a manufacturing process of the protein imprinted polymer film is provided, the term "template molecules" means target molecular or its antibody.

As used herein, when a specific definition is not provided, the term "to extract" herein means to remove.

One preferred embodiment of the invention is a protein imprinted polymer film. In this embodiment, protein imprinted polymer film is producing by creating the imprinted film by imprinting the target proteins onto the film to create nanocavities of the target proteins, which can be reused to reduce the cost, by examining the interaction force between the imprinting template and the target proteins and monitoring the dynamics of the bonds between the protein molecules. The Imprinting template comprises a plurality of imprinted nanocavities with unified orientation and distribution formed by removing a plurality of target proteins from a polymer film, wherein the target proteins are bound to a plurality of antibodies on a gold layer of a first substrate. In addition, it is possible to enhance specificity and improve the structure of the protein imprinted polymer film by mixing solvents having different volatility and changing the ratio thereof during the photopolymerization process.

The method of fabricating the C-reactive protein imprinted film, the technique used to measure its surface roughness with an atomic force microscope (AFM). The present invention will be explained in more detail referring to Examples below without intention of restricting the scope of the present invention.

EXAMPLE 1

Preparation of C-Reactive Protein Imprinted Polymer Film 1-1 Imprinting Template The process of the present invention is divided into two main parts: the imprinting template and protein imprinted polymer film. One embodiment of the present invention uses a four-inch glass wafer as the imprinting template; the glass wafer surface is vacuum coated with a 400 nm gold layer and a 25 nm adhesion layer (Ti) by using an E-gun.

Figure 1:
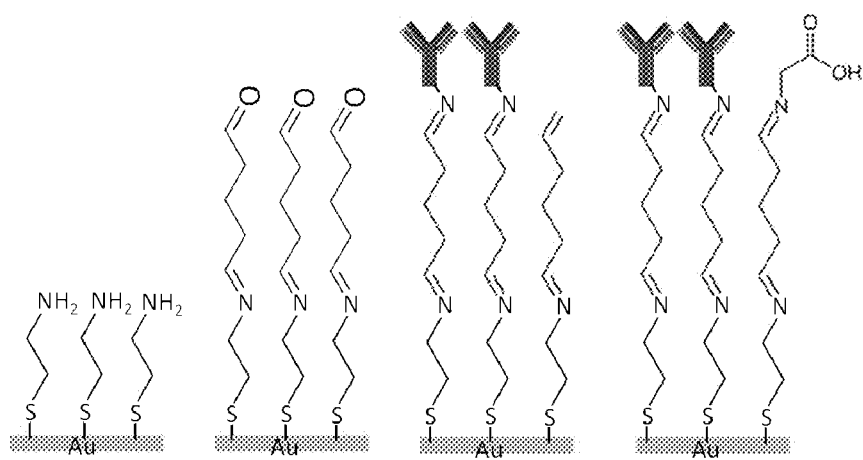
FIG. 1 illustrates the steps of modifying the imprinting template surface with cysteamine-glutaraldehyde.

The surface of the imprinting template is modified by cysteamine-glutaraldehyde method; as shown in FIG. 1, the first modification agent is cysteamine represented by the formula (1):

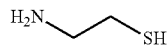

Formula (1)

By using the electron pair of the sulfur bond, located at one end of the cysteamine, with the empty orbit of the outer electron shell of a gold atom, a stable coordination complex is formed. This gold-sulfur bond (polar covalent bond) is as a coordinate covalent bond. The reaction is shown by the following chemical equation:

$$R\text{—}SH + Au \rightarrow R\text{—}S\text{—}Au + 1/2 H_2$$

Even though gold is very stable, and has a high activation energy; the gold surface easily adsorbs hydrocarbons in the air. A thiol molecule, having a high bonding energy, can be used to replace the hydrocarbons adsorbed on the gold surface, then forming a stable self-assembling molecular monolayer film.

The second modification reagent is glutaraldehyde represented by the formula (2):

Formula (2)

By bonding the aldehyde group, located on one end of the glutaraldehyde, with the amino group, located on the none bonding end of the cysteamine, a schiff base is formed. The aldehyde group, located on the other end of glutaraldehyde, can bind with the amino groups on a bio-molecular antibody; the aldehyde group that has not bound to antibody is bound to glycine represented by the formula (3), to avoid non-specific adsorption with the target molecules.

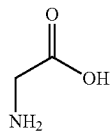

Formula (3)

Therefore, bonding a cystemine molecular to a surface of the gold elecrode by forming a gold-sulfur bond, and bonding the aldehyde group of the glutaraldehyde to the amino group of a cystamin for forming a schiff base, finally bonding the other end of the glutaraldehyde to the amino group of an antibody, the antibody is eventually bound to the gold surface.

Figure 2:
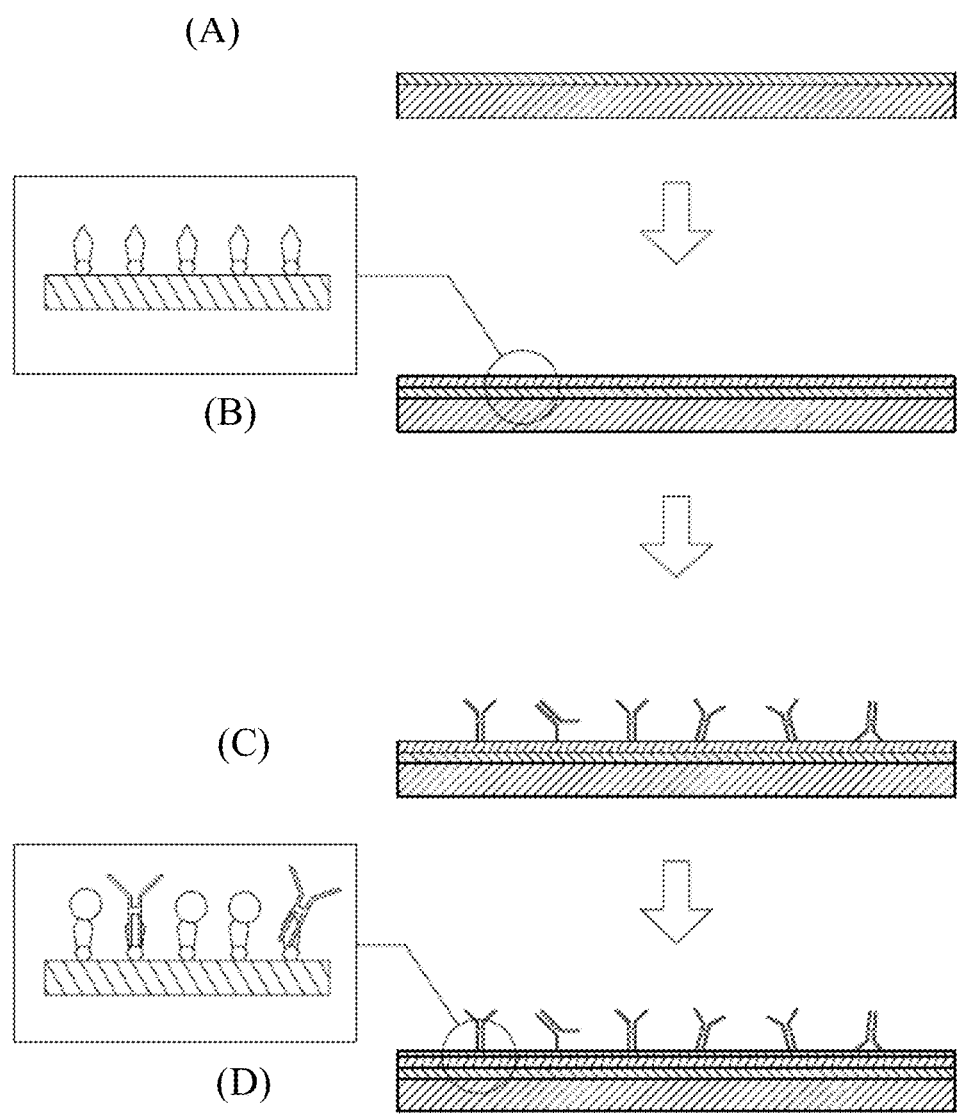
FIG. 2 illustrates the steps of manufacturing the modified surface of the imprinting template.

FIG. 2 illustrates the steps of modificating the surface of the imprinting template of the present invention. The steps of the surface modification of the imprinting template are described as follows. The volume of each solution in each step is 20 ml, and ultrapure water is used between each step for washing:

First, a gold-plated glass template is provided as shown in FIG. 2(A). The template is immersed in 18 mM cystamine aqueous solution for 8 hours (in the dark at room temperature), and washed with ultrapure water. Then, the template is immersed in a 12% glutaraldehyde aqueous solution for 8 hours, and washed with ultrapure water, as shown in FIG. 2(B).

Second, the template is immersed in a phosphate buffer solution (PBS) with 50 μg/ml C-reactive protein antibodies at room temperature for 1 hour to form the state as shown in FIG. 2(C). Then, the template is immersed in a phosphateacid buffer solution with 0.02 M glycine for 1.5 hours. Each antibody does not bind to the glutaraldehyde when an aldehyde group of the glutaraldehyde is bound to glycine as shown in FIG. 2(D).

By following the above steps, the antibody array template of the present invention is fabricated, wherein the C-reactive protein antibody (Anti-CRP) used in one embodiment of the present invention is purchased from SIGMA-ALDRICH, which is CRP-8, a kind of C-reacting protein monoclonal antibody, produced from mouse ascites; and the original concentration is 28.5 mg/ml.

The Bonding Time of the Modification Agent

The forked part of the finger electrode of the electrochemical impedance spectroscopy analyzer is put into the modification agent of the first step; monitor for reading once each 5 minutes from the beginning of the modification process. Monitor each step and optimize the process of the modification. The result can be variable since the condition of the modification process is affected by many fabrication parameters, thus the analysis is performed multiple times, and the maximum time is measured that is needed to reach a stable surface capacitance.

The results of the electrochemical impedance spectroscopy (EIS) shows that the time to reach a stabilized surface capacitance, wherein cysteamine needs 8 hours, glutaraldehyde needs 8 hours, C-reactive protein antibody needs 0.8 hours, glycine needs 1.5 hours. Thus, the optimized time needed for the immersed step of cysteamine is 8 hours, the time for glutaraldehyde is 8 hours, the time for C-reactive protein antibody is 1 hour, and the time for glycine for 1.5 hours.

According to the surface modification process of the present invention, each C-reactive protein antibody is connected to a C-reactive protein and a functional monomer O-4-nitrophenylphosphorylchonline (O-4NPPC) to form a precomposite, which can be polymerized with a cross-linker to form a polymer. The result of the EIS shows that the time needed to reach a stabilized surface capacitance for the antibody connecting with the C-reactive protein and O-4NPPC is 1.5 and 3 hours respectively.

The Number of Washings of the Modification Process

Between each step of the imprinting template modification process, ultrapure water is used for washing the gold surface to remove unbound molecules. This is to ensure that the modifying molecules are adsorbed separately and stocked up layer by layer. Each washing process is done by placing the plate into ultrapure water and shaking it back and forth. The process is repeated several times until the gold plate reaches a stabilized surface capacitance, this means that all the unbound molecules are washed away. By using EIS at 12 Hz to monitor the impedance of the gold surface and converting it into capacitance to estimate the state of the modifying molecule on the gold surface. By analyzing the changing curve of capacitance over the number of washings for each modifying molecule, from cysteamine, glutaraldehyde, C-reactive protein antibody to glycine, the cysteamine and glycine in powder form take more number of washings to reach a stabilized surface capacitance, because it formation makes it harder to wash away (cysteamine take about 8 times; glycine takes about 6 times). Glutaraldehyde and C-reactive protein antibody on the other hand are formed as liquid are easier to wash away, and the surface capacitance reaches stable after 3 times of washing.

Synthesis of the Protein Imprinted Polymer Film

The protein molecule imprinting technique of the present invention comprises three steps of combination, polymerization, and extraction in order. The purpose of the combination step is to mix the functional monomer and the template molecule, using the interaction force between them to combine and form a pre-polymerization complex, the interaction force may be a covalent bond or non-covalent bond. The polymerization is done by mixing the initiator, cross-linker into the pre-polymerization complex; the initiator is excited by light or heat to start polymerization, then the cross-linker is used to link with the functional monomers and form a polymer substrate. The extraction step is to remove the template molecules to form a plurality of nanocavities, which can be used to capture target molecules, and finally the molecule imprinted polymer film is obtained that can be used to identify a specific molecule such as the template molecule.

In addition, the protein imprinted polymer film of the present invention uses C-reactive protein (CRP) as the template molecule, which micro-contacts with the polymer film. Ultraviolet light is used to micro-curing the protein imprinted polymer film, while a designed photomasks is used to define its shape and size. FIG. 3 illustrates the steps of manufacturing the C-reactive protein imprinted polymer film of the C-reactive protein microchip system.

1. Refer to the left side of (A) part of FIG. 3A (i.e. the antibody array template of FIG. 2(D)), the above antibody array template is immersed in a phosphate buffer solution with 5 μg/ml C-reactive protein at room temperature for 1.5 hours. Then, the C-reactive protein is connected to the antibody as a result, as shown the middle of (A) part of FIG. 3A.

2. Refer to the right side of (A) part of FIG. 3A, the template is immersed in a ultrapure water solution with 0.1 mg/ml O-4-nitrophenylcholine and 2 mM calcium ($Ca^{2+}$) at room temperature for 3 hours to form a pre-polymerization complex.

3. Refer to (B) part of FIG. 3A, after adding molecular sieves into the cross-linker (dimethacrylate, PEG400DMA) to remove the inhibitors, and the cross-linker is mixed with the initiator (2,2'-dimethoxyl-2-phenyl acetophenone, DMPA) to form a mixed solution with the molar ratio of the cross-linker to the initiator from 600:1 to 640:1. Drip the mixed solution onto another cleaned 4-inch glass wafer and cover it by micro-contacting with the above template.

Figure 4:
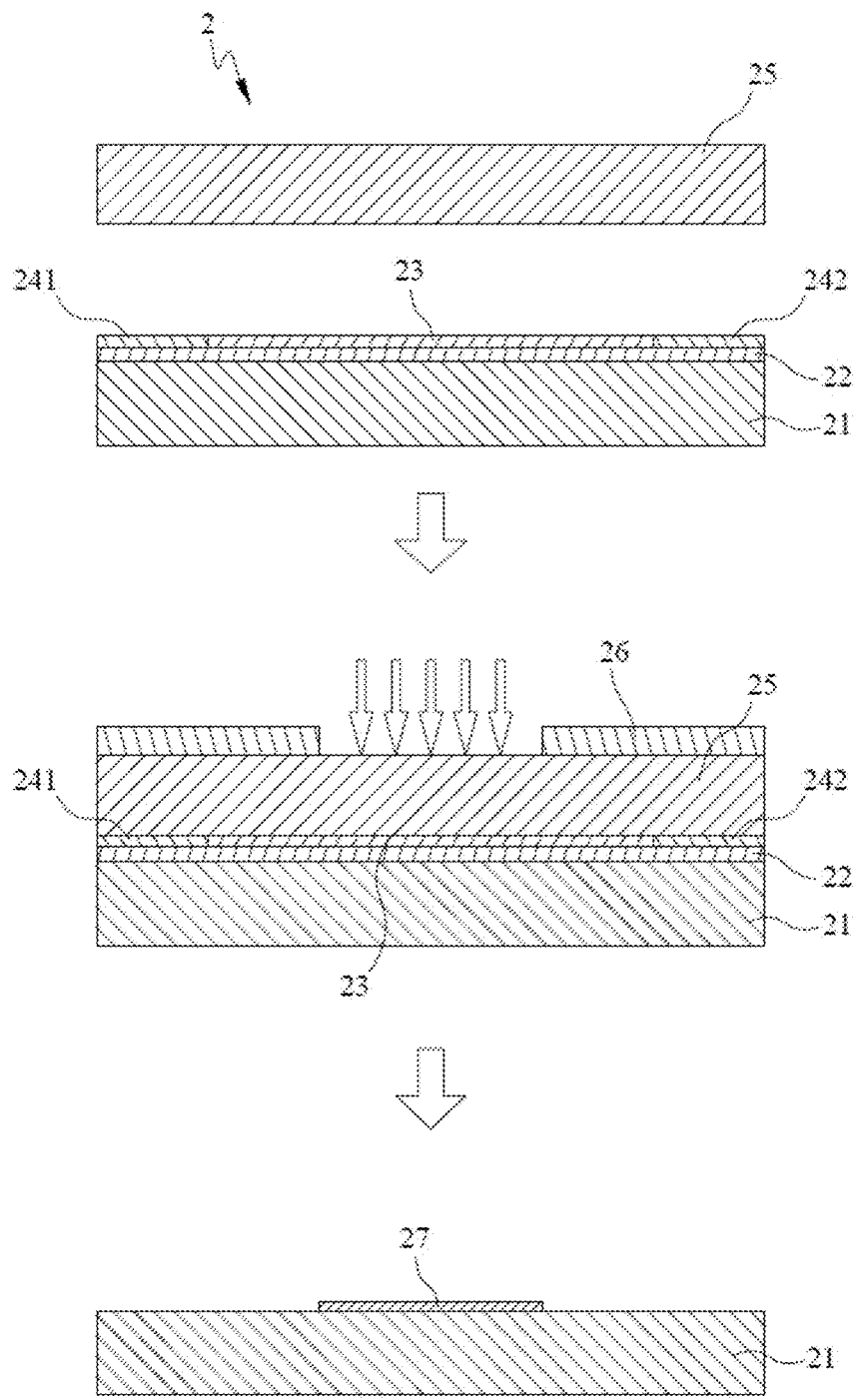
FIG. 4 illustrates the steps of the photopolymerization patterning process of the C-reactive protein imprinted film (PIP or AIP).

4. FIG. 4 illustrate the process of photopolymerization of the C-reactive protein imprinted polymer film. The template 21 is covered by functional monomer 22 and then covered by gaskets 241, 242. The space between gaskets 241, 242 is filled with the mixed solution 23 consisted of the cross-linker and the initiator, and then covered by a glass wafer 25, wherein the gasket is a 25 μm thick imprinting polymer film. The sample 2 is placed in an exposure apparatus with paralleled UV (I-line, 365 nm, optical intensity is about 6.4 $mW/cm^2$, parallel light), and the exposure time is about 300 seconds. The mask 26 is used to define the size and shape of the film.

5. Refer to (C) part of FIG. 3A, after completing the polymerization, the C-reactive protein imprinted polymer film is immersed in a mixed solution of 10% (w/v) sodium dodecyl sulfate (SDS) and 10% (v/v) acetic acid, and vibrated with ultrasonic for 30 minutes to extract the template molecules (CRP), thus the C-reactive protein imprinted polymer film is obtained.

Figure 3A:
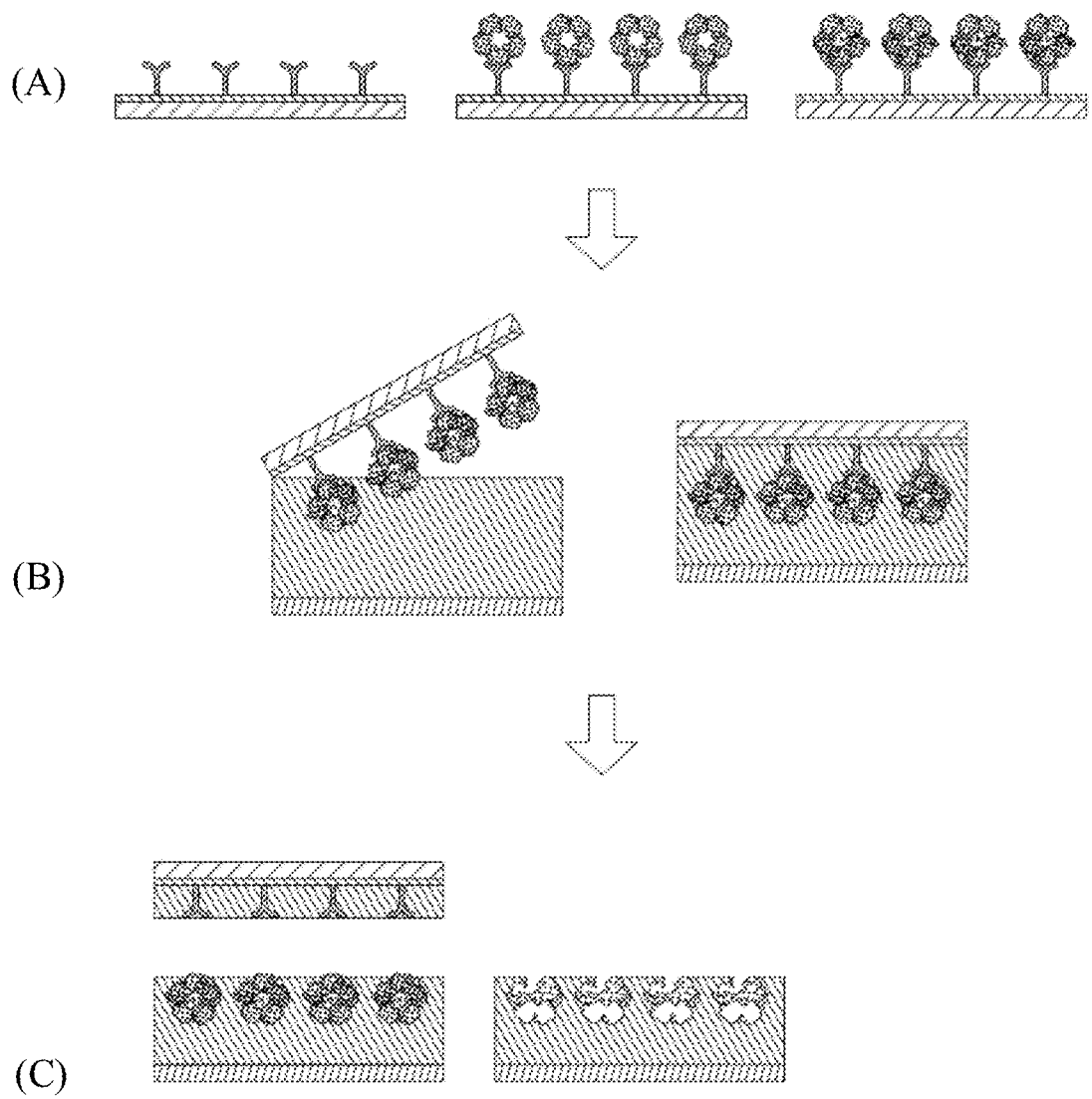
FIG. 3A illustrates the steps of manufacturing the C-reactive protein imprinted film (PIP).
Figure 3B:
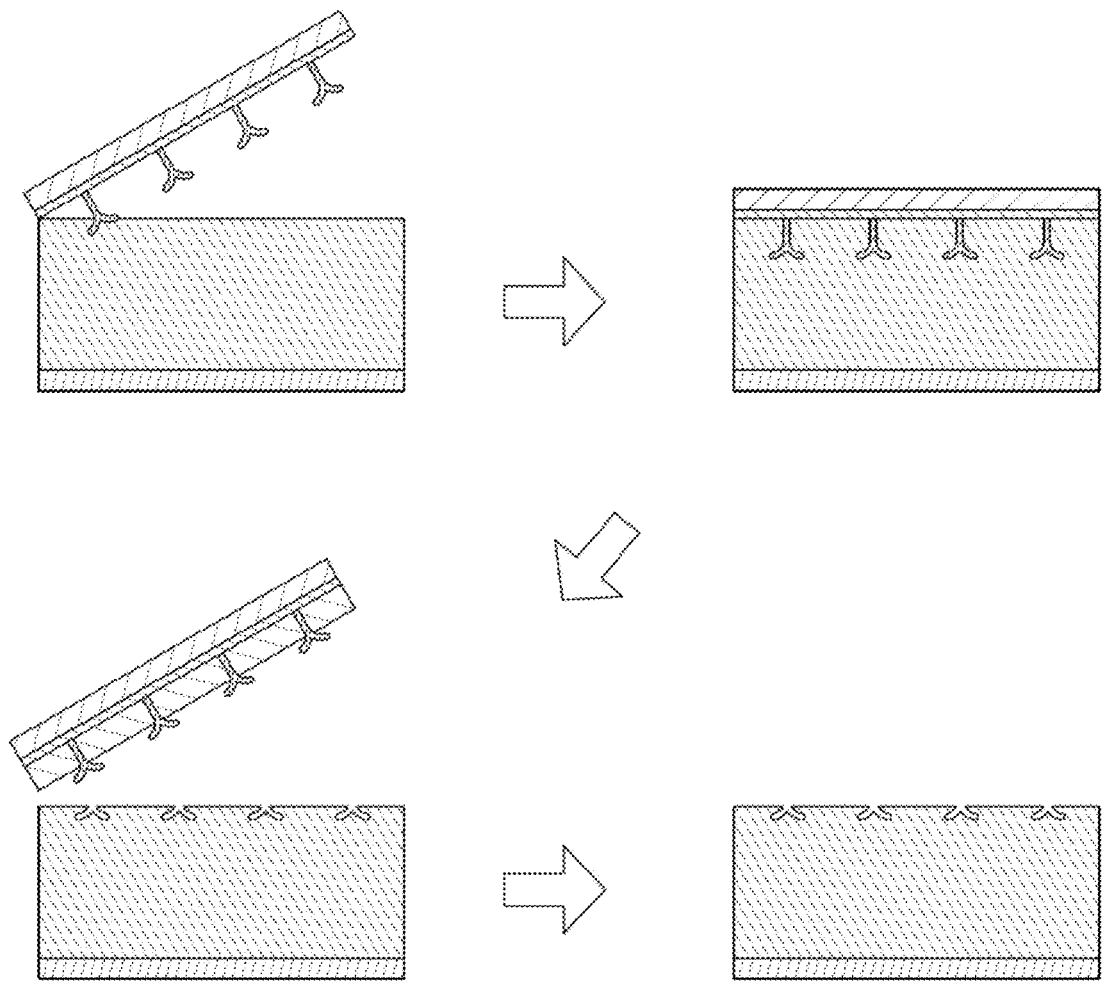
FIG. 3B illustrates the steps of manufacturing the C-reactive protein imprinted film (AIP).

The middle of (A) part of FIG. 3A illustrates a two-layer template, wherein one is an antibody template and the other is a C-reactive protein template. However, in one preferred embodiment, only one antibody template can be used to produce the protein imprinted polymer film, as shown in FIG. 3B. In another embodiment of the present invention, an antibody imprinted film (AIP) 27 of FIG. 4 has nanocavities imprinted by antibodies. The AIP can use the inverse bond structure of the antibody to capture the target proteins in a sample. By using the AIP, the cost can be significantly reduced compared to the two-layer template.

EXAMPLE 2

Measure the Surface of the CRP Imprinted Film by AFM

Atomic force microscope (AFM) uses a micro-cantilever which has a small tip on its front-end, by sensing its vibration, AFM can monitor interaction forces with the sample, such as mechanical contact force, Van der Waals forces, chemical bonds, electrostatic force, and magnetic force etc. The AFM uses laser to mark the front end of the micro-cantilever, and uses photodiode to detect its refection. When the micro-cantilever shifts, the refection shifts also, and is detected by the photodiode. By the shift distance, the strength of the interaction force between the sample and the tip can be determined. Therefore, AFM can be measured a conductor or a non-conductor samples, and the accuracy can achieved atom scale.

There are four sample films: NIP (non-imprinted polymer), AIP (antibody imprinted polymer) of the present invention, PIP with unified orientation and distribution (protein imprinted of polymer) of the present invention and PIP with random orientation and random distribution. NIP only adds the initiator and the cross-linker; it is only a pure polymer material that is used to test the nonspecific adsorption force between polymers and biological molecules. AIP is fabricated by micro-contacting the polymer film with the imprinting temple, which uses antibodies as the template molecule; compared to PIP, it skips the step that bonds the C-reactive protein to the imprinting template, thus the imprinted film has nanocavities of the antibody instead of the C-reactive protein. PIP is an imprinting template that bonds to antibodies and then bonds to the C-reactive proteins with unified orientation. The imprinting template is then micro-contacted to the polymer film to create nanocavities of the template molecules, as described in Example 1. PIP with random orientation and random distribution simulates the micro-contact method of Chou (P. C. Chou, J. Rick, T. C. Chou, C-reactive protein thin-film molecularly imprinted polymers formed using a micro-contact approach, Analytica Chimica Acta, Vol. 542, p 20-25, 2005), which modifies the imprinting template with cysteamine-glutaraldehyde, so that the surface is covered with aldehyde groups, which can cause nonspecific adsorption with biological molecules, and make the C-reactive proteins orient/distribute randomly on the imprinting template. The PIP with random orientation and random distribution is compared with the PIP with unified orientation. The following discussion refers to the protein imprinted polymer films of NIP, AIP of the present invention, PIP with random orientation and random distribution, PIP with non-optimized fabrication process and PIP with optimized fabrication process.

The PIP with optimized fabrication process has optimized orientation and distribution of the modified surface, optimized number of washings between each modification steps, optimized bonding time with each modification agent, and optimized a ratio of the mixture solution consisted of the cross-linker and the initiator. The detail steps are discussed in Example 1.

Figure 5:
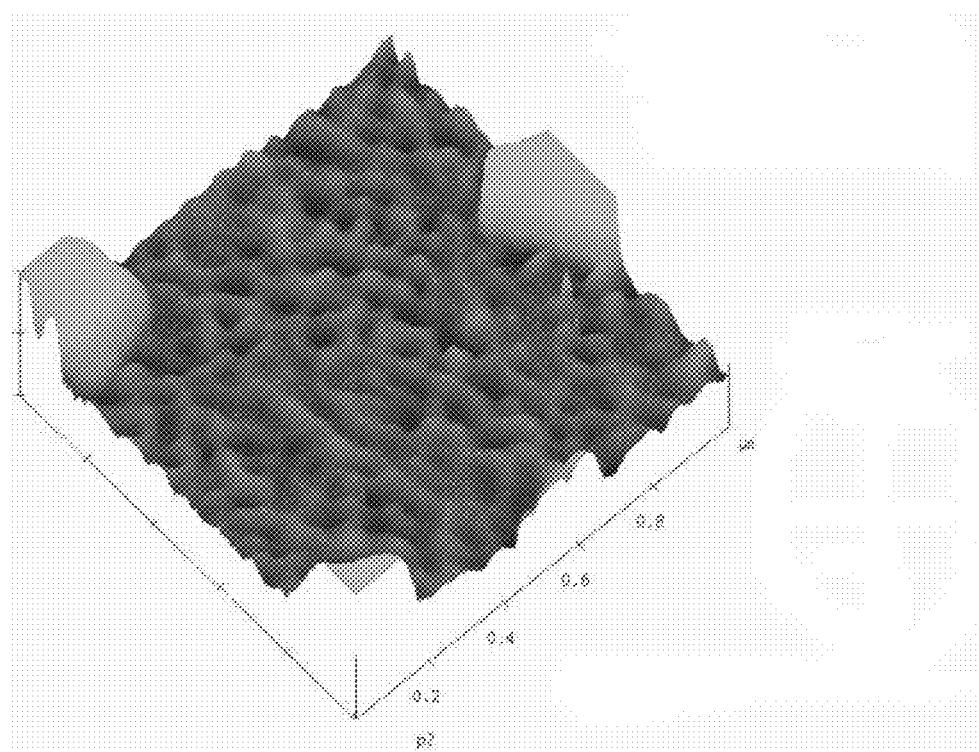
FIG. 5 is an AFM scanning image of the PIP with an optimized fabricating process.
Figure 6:
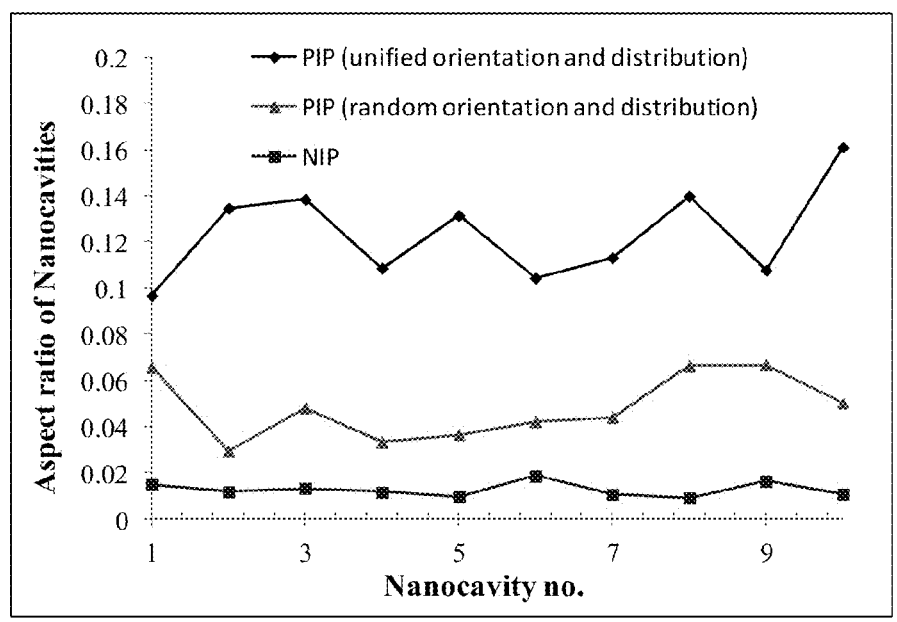
FIG. 6 is a diagram showing the aspect ratios of the imprinted nanocavities on NIP, PIP (random orientation and random distribution) and PIP (unified orientation and distribution).

FIG. 5 is the result of measuring a PIP (unified orientation and distribution) with optimized fabricating process with an AFM. The root mean square of the undulation is 16.826 nm, which is the largest value of all the sample templates (the root mean square is 0.29 nm with NIP, 3.117 nm with AIP, and 2.768 with PIP (random orientation and random distribution). The aspect ratios of the imprinted nanocavities on NIP, PIP (random orientation and random distribution) and PIP (unified orientation and distribution) are compared in FIG. 6. For NIP, the aspect ratios of the nanocavities on the membrane surfaces are less than 0.018. For PIP (random orientation and random distribution), the aspect ratios of the nanocavities are between 0.029 and 0.067. For PIP (unified orientation and distribution), the aspect ratios of the nanocavities are between 0.097 and 0.161. The well-aligned nanocavities of plastic antibody films, which are specific recognition sites formed by the template molecules, exhibit higher anisotropy ratio than the imprinted film with random orientation and distribution. Using antibodies not only can fix the orientation of the C-reactive protein but also lifts up the C-reactive protein, making it easier to be covered by the polymer during the micro-contact process. Compared with the PIP (random orientation and random distribution), the nanocavity of the optimized PIP is wider and deeper, the specific adsorption is also stronger. By optimizing the fabrication process of the PIP, the completeness of the nanocavities on the imprinted polymer film is improved.

To analysis the relationship between the AFM tip and the imprinting templates, and/or polymer film, the AFM tip is divided into three types: a golden tip, an antibody tip, and a CRP tip by the above gold-plated surface modification process. The imprinting template is also divided into three types: a gold surface, a cysteamine-glutaraldehyde modified surface, and a C-reactive protein modified surface. The film is divided into five kinds of polymer film such as NIP, AIP, PIP (random orientation and random distribution), pre-optimized PIP (unified orientation and distribution) and the optimized PIP (unified orientation and distribution).

The template is mainly used to analyze the interaction force between the antibody and C-reactive protein modified surface (specific adsorption force), antibody tip paired with the golden template surface and the golden tip paired with the C-reactive protein modified template surface stand for the two control groups of the weak interaction force. The antibody tip paired with the cysteamine-glutaraldehyde modified template surface or the antibody modified template surface stands for the test group of the non-specific adsorption.

The AFM tips can be divided into three types: the unmodified tip as the golden tip, the antibody bonded tip as the antibody tip, and the antibody and C-reactive protein bonded tip as the CRP tip.

As mentioned above, there is an interaction force between the AFM tip and the nanocavity of the polymer film. Thus, the negative viscous force generated when the AFM tip moves away from the surface is analyzed. By using of the AFM tips spring constant K and the shift distance X caused by viscous force, the interaction force F can be obtained from the following function:

$$F = -K \times X$$

The testing points are located as if they are on the crossing points of a 3 by 3 grid, each points separate 100 nm away from each other; the results are described below:

I. Imprinting Template

The experimental results show that the weak interaction force between the biological molecules (C-reactive protein antibody or the C-reative protein) and gold is about 10 nN. The non-specific adsorption between the antibody tip and the surface of cysteamine-glutaraldehyde template or the surface of the antibody template is about 20 nN. The specific adsorption force between the antibody and the C-reactive protein is about 30 nN. Since C-reactive protein antibody and C-reactive protein have multiple ligands making them easier to bind with others, the background weak interaction force in the control group is slightly stronger, but the difference between specific and non-specific adsorption is still significant.

II. Protein Imprinted Polymer

Figure 7:
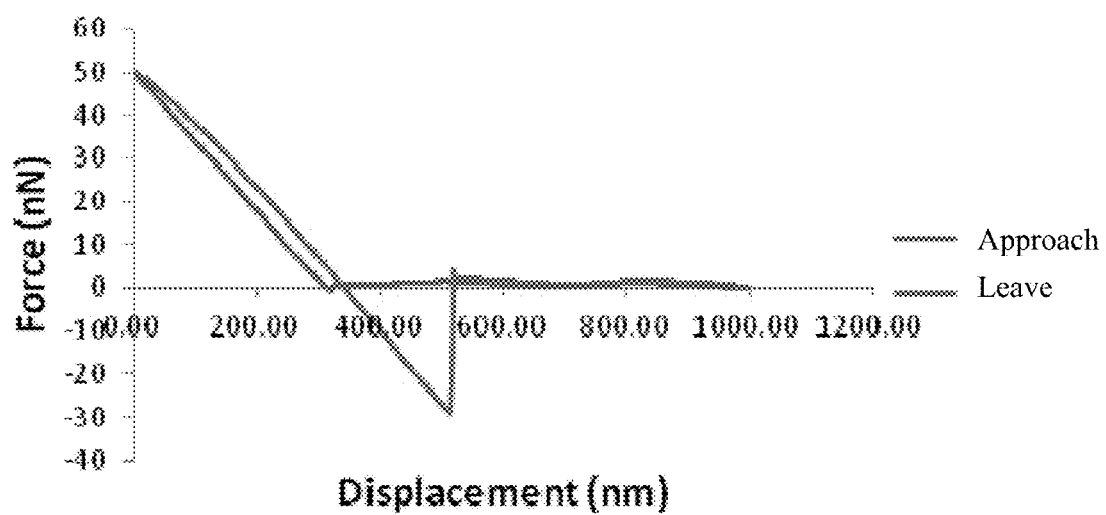
FIG. 7 is a diagram showing the relationship between the interaction force and distance between the C-reactive protein antibodies tip and the C-reactive protein imprinted film surface.

The experimental results show that the non-specific adsorption between C-reactive protein antibody and NIP is about 11.75 nN, slightly larger than the background weak interaction force, indicating that non-specific adsorption of the cross-linker is not significant. The interaction force between the C-reactive protein antibody and the AIP/PIP (random orientation and random distribution) is close to 20 nN, similar to the non-specific adsorption between the antibody tip and the cysteamine-glutaraldehyde template surface or antibody template surface, showing no significance in specific adsorption. The interaction force between the C-reactive protein antibody and the pre-optimized PIP film is only slightly larger than 20 nN, showing there is no obvious specific adsorption between them. FIG. 7 illustrates the relationship of the interaction force and distance in the C-reactive protein imprinting template (i.e. the optimized PIP film) by an AFM with a C-reactive protein antibody tip. The interaction force between the C-reactive protein antibody and PIP film is about 30 nN, which is almost the same as the interaction force between C-reactive protein antibody and C-reactive protein, showing a significant specific adsorption force, only with uneven orientation and distribution. Thus if the orientation and distribution of the imprinted nanocavities is improved, the specific adsorption should be enhanced.

The weak interaction force between the C-reactive protein antibody tip and the gold layer is about 10 nN; the non-specific adsorption between the C-reactive protein antibody tip and the cysteamine-glutaraldehyde template surface or C-reactive protein antibody template surface is about 20 nN. The specific adsorption force between the C-reactive protein antibody and the C-reactive protein is about 30 nN; the non-specific adsorption between the C-reactive protein antibody and NIP is about 11.75 nN, only slightly stronger than the background week interaction force, showing no significant non-specific adsorption. The interaction force between the C-reactive protein antibody and AIP/PIP (random orientation and random distribution) is close to 20 nN, similar to the non-specific adsorption in the imprinting template. The interaction force between the C-reactive protein antibody and the pre-optimized PIP film is only slightly larger than 20 nN. The interaction force between the C-reactive protein antibody and the optimized PIP is about 30 nN (29.36±4.90 nN), which is almost the same as the interaction force between the C-reactive protein antibody and the C-reactive protein, showing a significant specific adsorption force. The specific interaction force of the optimized PIP (up to 14.28 nN, about 87% compared to nature antibodies) is similar to nature antibodies.

To analyze if the PIP film of the invention is capable of adsorbing the target molecule, there is a control group that can represent the non-specific adsorption to the target molecule. A NIP (non-imprinted polymer) film without imprinted nanocavities is fabricated with the same method and material as the PIP film, and the adsorption amount of the NIP can stand for the amount of molecules adsorbed by non-specific adsorption. The real amount of specific adsorption should be the subtracting the adsorption of NIP from the adsorption of PIP. The steps of the examination are described as followed:

(1) There are two sample solutions at different concentrations, one with the concentration of 0.1 μg/ml and the other with 0.5 μg/ml. Each sample solution is injected into the micro-channel having a NIP film, a PIP film (random) or a PIP film. The volume of the camber is 1.032 μl, and the adsorption time is 10 seconds. Then, the detector detects and measures each sample solution concentration of the target molecules captured on the above imprinted film.

(2) By measuring each sample solution concentration, the amount of absorption of each film is calculated. The amount of absorption on PIP film and NIP film, by subtracting the two values, the specific absorption amount of the PIP film is obtained. The results of the measurement are shown in Table 1; the "ratio" means the value of the absorption amount of each film based on the NIP film.

TABLE 1

| | Specific adsorption force | | | | |
|---|---|---|---|---|---|
| Adsorption Amount | NIP (ng/mm$^2$) | AIP (ng/mm$^2$) | PIP-r (ng/mm$^2$) | PIP (ng/mm$^2$) | Antibody (ng/mm$^2$) |
| 0.1 μg/ml | 0.0028 | 0.0080 | 0.0088 | 0.0108 | 0.0108 |
| ratio | 1.00 | 2.87 | 3.17 | 3.87 | 3.87 |
| 0.5 μg/ml | 0.0121 | 0.0431 | 0.0473 | 0.0527 | 0.0582 |
| ratio | 1.00 | 3.56 | 3.91 | 4.35 | 4.81 |

Table 1 shows the adsorption force of the PIP film is very close to the nature antibody, followed by PIP-r, the AIP also shows good results.

In addition, the PIP film is immersed in three C-reactive protein solutions with different concentration of 0.1, 0.5 and 1 μg/ml. Compared with the results measured with the 1 μg/ml solution, the adsorption amount of the NIP (non-specific bonding) is significantly lower. The adsorption amount of the PIP and the antibody is 0.746 ng/cm$^2$ and 0.752 ng/cm$^2$ respectively, and the PIP/NIP and antibody/NIP is 5.33 and 5.37 respectively. The measured adsorption force of PIP is 0.75 ng/cm$^2$. The measured adsorption force of NIP is 0.14 ng/cm$^2$. Based on a 1 cm$^2$ surface area, the adsorption force is 0.61 ng, the PIP/NIP is about 5. The adsorbion force of the target proteins of the optimized PIP (about 99% compared to nature antibodies) is similar to nature antibodies.

EXAMPLE 3

C-Reactive Protein Microchip System

To measure the concentration of the C-reactive protein in a sample, high-performance liquid chromatography (HPLC) method is often used in academic researches. The concentration of the sample must be above 100 μg/ml to accurately analyze its composition in actual practices. However, the concentration of the C-reactive protein in a normal human body is bellow 8 μg/ml, therefore the application of the HPLC method in a clinical environment is difficult and impractical.

In clinical research, enzyme-linked immunoassay (ELISA) is a method to measure the concentration of the C-reactive protein in a sample. The sample need to be serial diluted to a final concentration bellow 1000 pg/ml. The concentration of a clinical sample is about 1-15 μg/ml, which requires to be diluted to one thousandth of its original concentration. This process is highly vulnerable due to human negligence or contamination.

Figure 8:
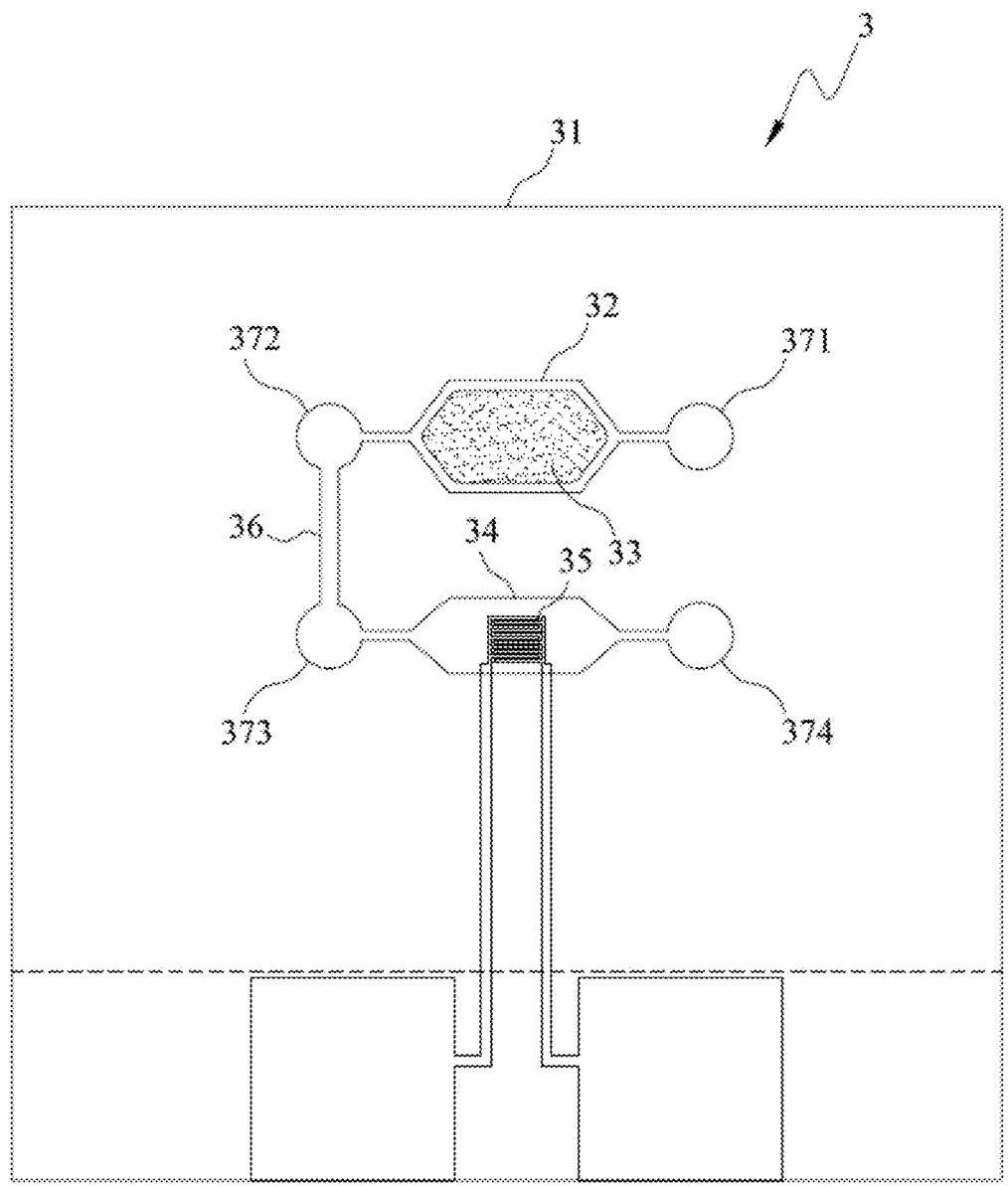
FIG. 8 illustrates a top view of the body of the C-reactive protein microchip system.
Figure 9:
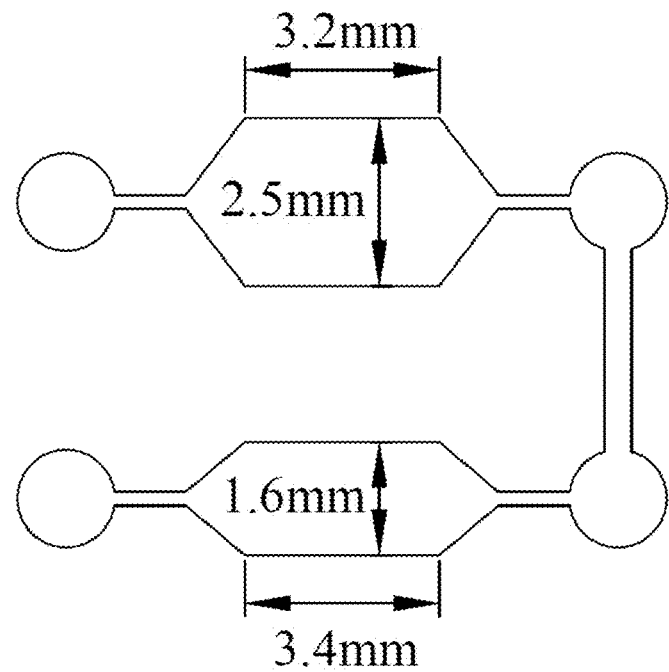
FIG. 9 illustrates the specification of the first chamber and the second chamber of the C-reactive protein microchip system.

The C-reactive protein microchip system is shown in FIG. 8. The C-reactive protein microchip system 3 comprises a body 31, which may be shaped into a panel, the section below the dotted line can be made thinner, making it easier to plug into a detector 38 (not shown) slot. The body 31 comprises a first chamber 32 including a C-reactive protein imprinted polymer film 33, and the first chamber 32 is connected to a first portal 371 and a second portal 372 respectively, when a sample comprising C-reactive proteins is injected into the first portal 371 and flowing through the C-reactive protein antibody imprinted polymer film 33, flowing out of the first chamber from the second portal 372. A second chamber 34 including a sensing electrode 35, and the second chamber 34 is connected to a third portal 373 and a fourth portal 374 respectively, when an extracting solvent is injected into the first portal 371 to extract the C-reactive proteins being captured by the imprinted nanocavities, flowing into the second chamber 34 via the third portal 373, flowing out of the second chamber 34 from the fourth portal 374. The C-reactive protein microchip system 3 also includes a detector 38 (not shown in the figure), it detects a potential change of the sensing electrode 35 and generates a detecting result based on the detected potential change. FIG. 9 illustrates a scheme diagram of the first and second chambers, and the heights of all micro-channels are 100 μm.

When the sample comprising C-reactive proteins is injected into the first chamber 32 via the first portal 371 and flow through the C-reactive protein antibody imprinted polymer film 33 located in the first chamber 32, some of the C-reactive proteins will be captured by the imprinted nanocavities with unified orientation and distribution (the film 33 can be PIP with unified orientation and distribution or AIP with unified orientation and distribution), flowing out of the first chamber from the second portal 372. Then a phosphate buffer solution is used to wash through portal 371 and 372 to remove non-specific adsorbed materials. When an extracting solvent (10% sodium dodecyl sulfate and 10% acetic acid) is injected into the first portal 371 to extract the C-reactive proteins being captured by the imprinted nanocavities, flowing into the second chamber 34 via the third portal 373 for detecting a potential change of the sensing electrode 35 and generating a detecting result (dynamic discharge) based on the detected potential change, then flowing out of the second chamber from the fourth portal 374. The absorption time of the imprinted polymer film is 60 seconds and the response time of the sensing electrode is 10 seconds.

Another embodiment of the present invention pours in 1 μl of the test solution from portal 371 to the first chamber 32 for 60 seconds, lets the C-reactive protein in the test solution adsorbed to the C-reactive protein imprinted film 33, then direct the test solution into the second chamber 34, analyze the concentration 10 seconds later through the sensing electrode 35 (LCR measurement capacitor).

In addition, if the sensing electrode is in the low frequency, the impedance-frequency curve is more related to the state of the electrode surface. The capacitance value of the electrode is changed when the electrode surface is bonded with antibodies and C-reactive proteins to form an equivalent circuit as an electric double layer capacitors, thus the low frequency (12 Hz) component is analyzed.

Dynamic Capacitance Sensing Mechanism

The C-reactive proteins captured by the PIP film are extracted by SDS solvent and detected by the sensing electrode. The sensing electrode catches C-reactive proteins by its vulcanized or antibody modified surface, and measures the concentration of C-reactive proteins by monitoring change of dynamic capacitance of the electrode surface and referring to the calibration curve.

The circuit of the dynamic capacitance sensing method can be applied to a portable devices or a handheld devices. Before measuring the dynamic capacitance, the system is simplified into an equivalent system, making it easier to analyze. The calculated results of the dynamic capacitance sensing system are the system capacitance and the system resistance; the gold electrode and its modified surface molecules can be simplified to an equivalent system capacitor and an equivalent system resistor. With the assumption of this simplified system structure, we can assume the calculate system capacitor and the equivalent system resistor as if they are the double layer capacitor and leakage resistor of the dynamic capacitance measurement system. Based on the discharge curve, the time coefficient, capacitance and resistance value of the system are calculated to achieve the goal of measuring the dynamic capacitance.

Figure 10:
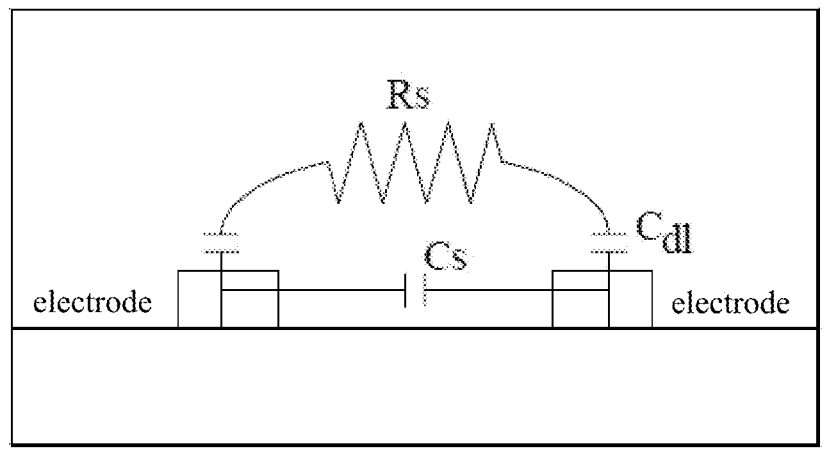
FIG. 10 illustrates an equivalent circuit analysis of bare gold electrode.
Figure 10:
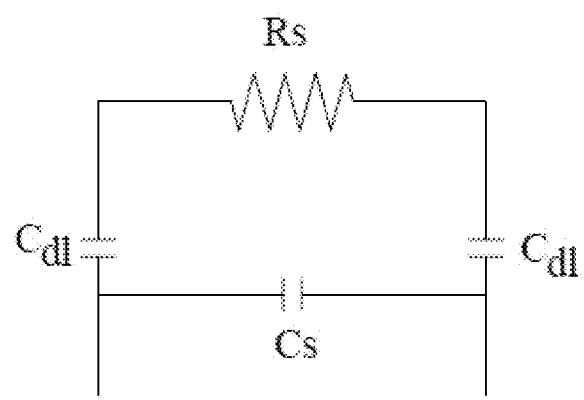

According to the above description, the first step is to analyze the equivalent circuit of the electrode and simplify the system. The equivalent circuit analysis of the sensing electrode is divided into two parts: the bare gold electrode and its modified surface. The analysis results for the bare gold electrode is shown in FIG. 10, the symbol $C_s$, $R_s$ and $C_{dl}$ each represents an electrolyte capacitor, an electrolyte resistor and a double layer capacitor respectively.

The fabrication method of gold electrode with modified surface is as follows: use a glass or plastic plate as a template, vacuum evaporation a 400 nm gold layer and a 25 nm Chromium adhesion layer with an E-gun. The gold-plated wafer is made into be a finger electrode by the photolithigraphy process. Then let antibody bind to the surface of finger electrode by the template modification process.

Figure 11:
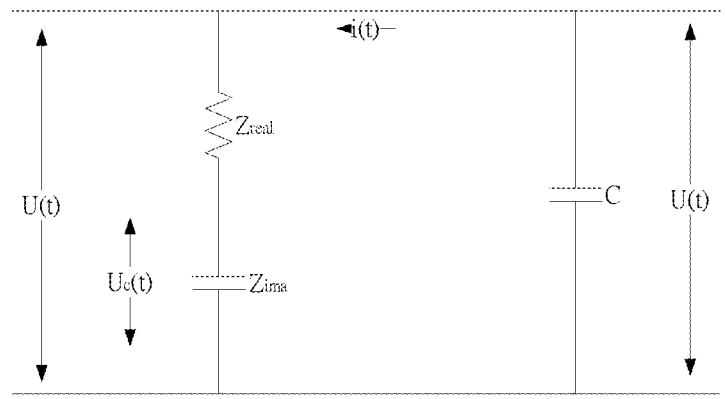
FIG. 11 illustrates the relationship between the external circuitry on the gold electrode, which has its surface modified, and the sensing electrode.

The modified surface of the gold electrode can be simplified as an equivalent capacitor. When the proteins are adsorbed on the surface, the capacitance of the equivalent capacitor is changed. The potential change is caused by dynamic balancing relationship between potential energy of an equivalent circuit and a sensing circuit of the detector, and the potential change is related to an amount of the C-reactive proteins contained in the extracting solvent, wherein the equivalent circuit is formed with the sensing electrode and the extracting solvent in the second chamber. Please refer to FIG. 11, the C is capacitor; $Z_{real}$ and $Z_{ima}$ are the real part and imaginary part of the impedance; i(t) is current; $U_c(t)$ is the potential energy of imaginary part of the impedance; U(t) is the measured potential.

Figure 12:
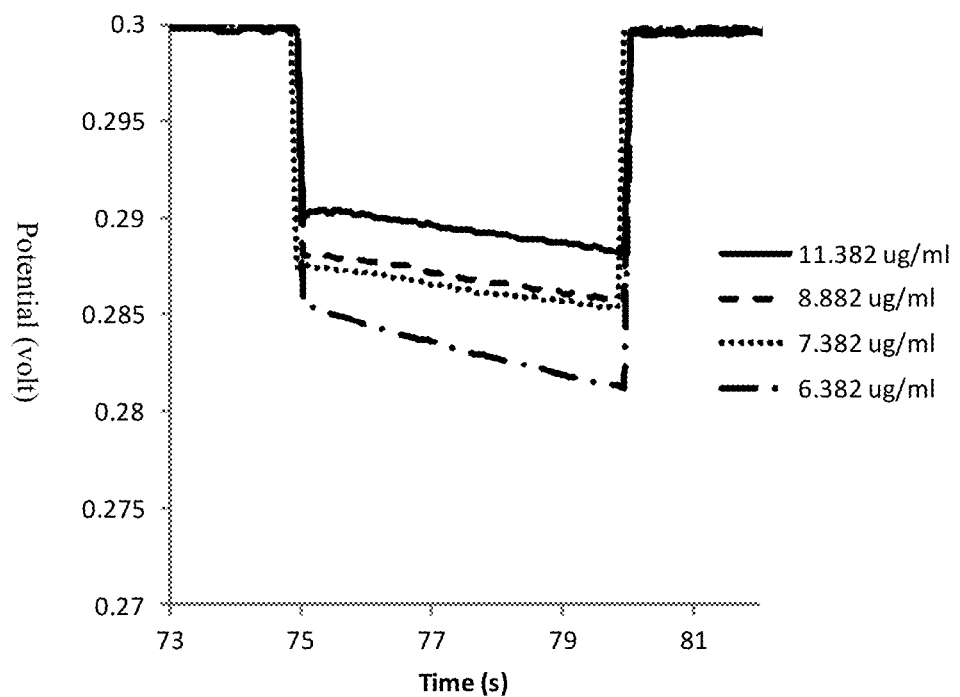
FIG. 12 illustrates the dynamic potential change of the C-reactive protein samples at different concentrations.
Figure 13:
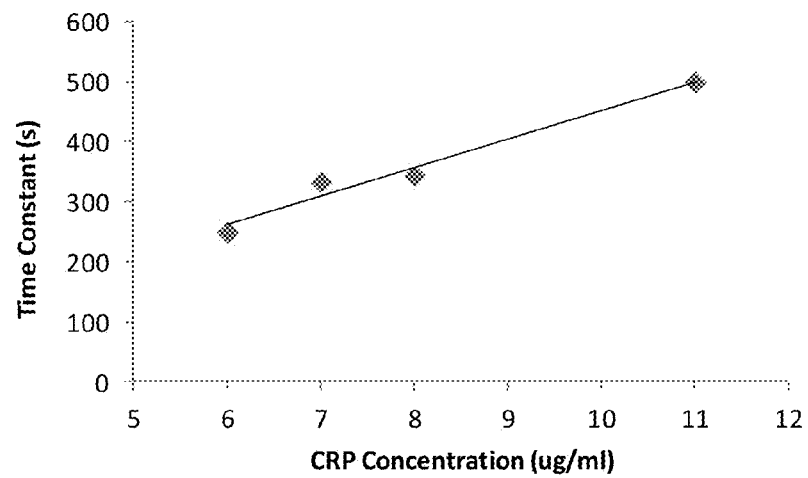
FIG. 13 illustrates the relationship between the time coefficient of the potential curve of FIG. 10 and different C-reactive protein concentrations.
Figure 14:
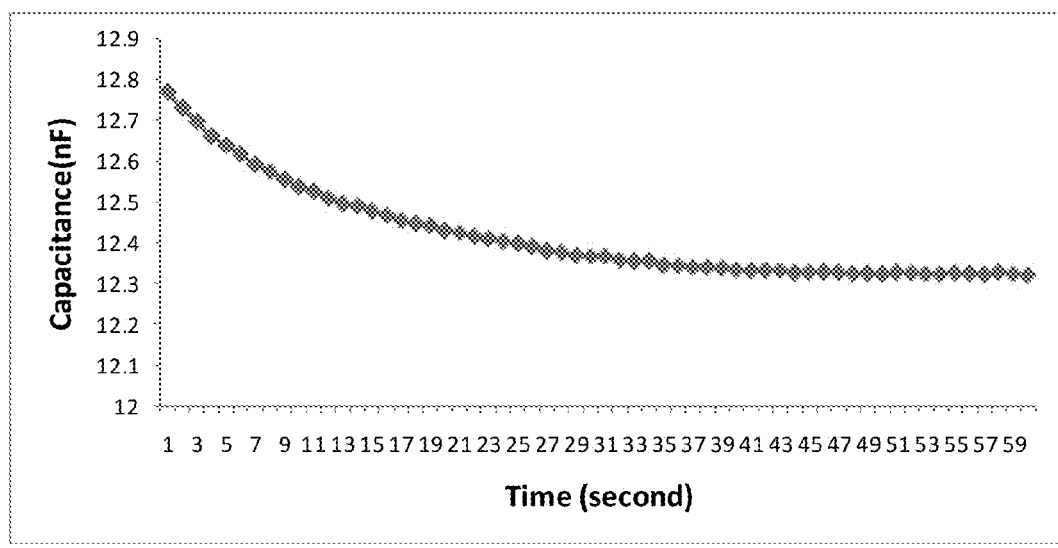
FIG. 14 illustrates the surface capacitance change of the sensing electrode in the second chamber of the C-reactive protein microchip system.

Human Serum Examination:

The concentrations of the C-reactive proteins in human serum are 6.382, 7.382, 8.882, 11.382 μg/ml respectively. The C-reactive proteins captured by the PIP film are extracted by SDS solvent and detected by the sensing electrode. The sensing electrode catches C-reactive proteins by its vulcanized or antibody modified surface, and measures the concentration of C-reactive proteins by monitoring change of dynamic capacitance of the electrode surface as shown in FIG. 12. The C-reactive protein microchip system will start to detect the concentration of the C-reactive proteins at the 75th second and end at the 80th second. The depth of the micro-channel is 125 μm. The detecting result is determined by a time coefficient of the potential change at different C-reactive protein concentrations, as shown in FIG. 13. Please refer to FIG. 14, illustrates capacitance change curve of the electrode surface in the second chamber of C-reactive protein microchip system, adsorbing C-reactive protein at runtime. As shown in FIG. 14, the reaction time of the detector is about 10 seconds, compared to the cost of several hours (>2 hours) of the conventional ELISA analyze, C-reactive protein microchip system of the present invention reduces the examination time significantly. Besides, the C-reactive protein microchip system of the invention is label-free system, which detecting C-reactive protein without changing their bonding. Therefore, the detection process is very fast, total detection time can be less than 110 seconds. For further reduce total detection time from 110 seconds to 15 seconds, just adjusting the depth of the micro-channel from 125 μm to 30 μm.

Figure 15:
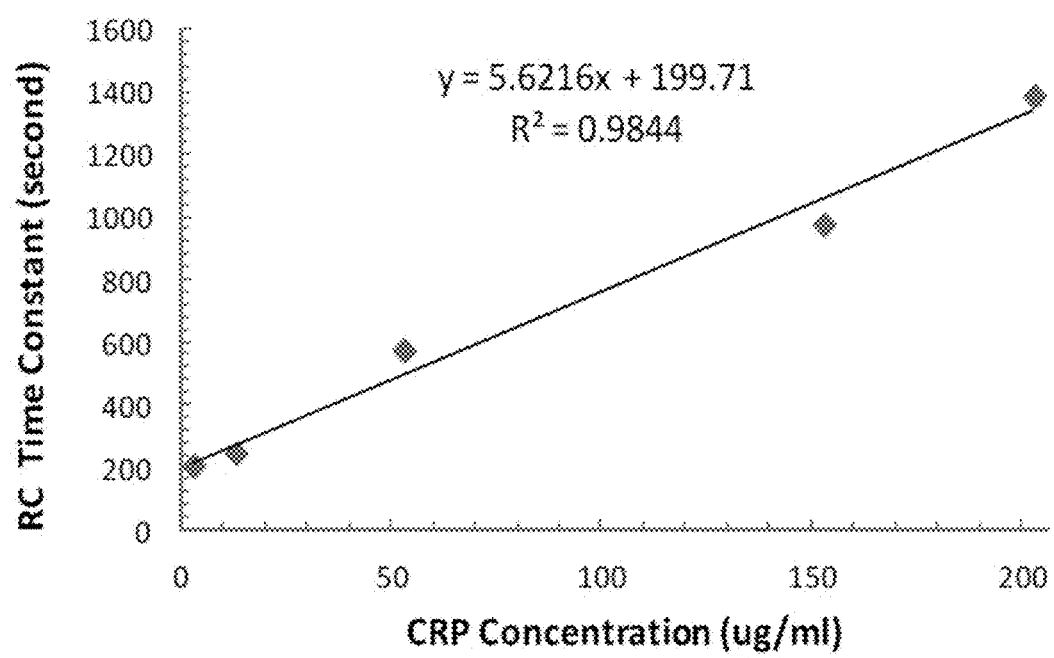
FIG. 15 illustrates the relationship between the time coefficient and C-reactive protein concentrations when the depth of the micro-channel is 30 µm.

Further shorting the depth of the micro-channel to 30 μm, the result as shown in FIG. 15, the linear part of the curve is from 2 μg/ml to 200 μg/ml, illustrates the concentration range of C-reactive protein can be detected is from 2 μg/ml to 200 μg/ml.

What is claimed is:

1. A C-reactive protein imprinted polymer film, comprising:
    a plurality of imprinted nanocavities with unified orientation and distribution formed by removing a plurality of C-reactive proteins from a polymer film, wherein the C-reactive proteins are bound to a plurality of antibodies on a modified surface of a first substrate.

2. The C-reactive protein imprinted polymer film of claim 1, wherein the modified surface of the first substrate is formed by a gold layer on the first substrate surface binding with cysteamine and glutaraldehyde in order.

3. The C-reactive protein imprinted polymer film of claim 2, wherein each antibody of the plurality of antibodies binds to an aldehyde group of the glutaraldehyde, which antibody does not bind to the glutaraldehyde when the aldehyde group is bound to glycine.

4. The C-reactive protein imprinted polymer film of claim 1, wherein the C-reactive proteins are connected to O-4-nitrophenylphosphoryl choline to form a plurality of precomposites which each micro-contacts with a composition on a second substrate, and the composition is consisted of a cross-linker and an initiator with the molar ratio of the cross-linker to the initiator from 600:1 to 640:1.

5. The C-reactive protein imprinted polymer film of claim 4, wherein the cross-linker is dimethacrylate, polyethylene glycol diacrylate or trimethylolpropane triacrylate; and the initiator is 2,2'-dimethoxy-2-phenyl acetophenone, 1-hydroxy-cyclohexyl-phenyl ketone, p-phenyl benzophenone or benzyl dimethyl ketal.

6. A C-reactive protein antibody imprinted polymer film, comprising:
a plurality of imprinted nanocavities with unified orientation and distribution formed by removing a plurality of C-reactive protein antibodies from a polymer film, wherein the C-reactive protein antibodies are bound to a modified surface of a first substrate.

7. The C-reactive protein antibody imprinted polymer film of claim 6, wherein the modified surface of the first substrate is formed by a gold layer on the first substrate surface binding with cysteamine and glutaraldehyde in order.

8. The C-reactive protein antibody imprinted polymer film of claim 7, wherein each antibody of the plurality of antibodies binds to an aldehyde group of the glutaraldehyde, which antibody does not bind to the glutaraldehyde when the aldehyde group is bound to glycine.

9. The C-reactive protein antibody imprinted polymer film of claim 6, wherein the C-reactive protein antibodies are connected to O-4-nitrophenylphosphorylcholine to form a plurality of precomposites which micro-contacts with a composition of a second substrate, and the composition is consisted of a cross-linker and an initiator with the molar ratio of the cross-linker to the initiator from 600:1 to 640:1.

10. The C-reactive protein antibody imprinted polymer film of claim 9, wherein the cross-linker is dimethacrylate, polyethylene glycol diacrylate or trimethylolpropane triacrylate; and the initiator is 2,2'-dimethoxy-2-phenyl acetophenone, 1-hydroxy-cyclohexyl-phenyl ketone, p-phenyl benzophenone or benzyl dimethyl ketal.

11. A C-reactive protein microchip system comprising:
a body, comprising:
a first chamber including a C-reactive protein imprinted polymer film having a plurality of imprinted nanocavities of claim 1 connected to a first portal and a second portal respectively, when a sample comprising C-reactive proteins is injected into the first portal and flowing through the C-reactive protein imprinted polymer film, flowing out of the first chamber from the second portal; and
a second chamber including a sensing electrode connected to a third portal and a fourth portal respectively, when an extracting solvent is injected into the first portal to extract the C-reactive proteins being captured by the imprinted nanocavities, flowing into the second chamber via the third portal, flowing out of the second chamber from the fourth portal; and
a detector, for detecting a potential change of the sensing electrode and generating a detecting result based on the detected potential change.

12. The C-reactive protein microchip system of claim 11, wherein the sensing electrode is a gold electrode.

13. The C-reactive protein microchip system of claim 11, wherein the sensing electrode is a finger electrode.

14. The C-reactive protein microchip system of claim 11, wherein the finger electrode is formed by a gold-plated plastic material processing photolithograph.

15. The C-reactive protein microchip system of claim 13, wherein the sensing electrode has a vulcanized surface or an antibody modified surface.

16. The C-reactive protein microchip system of claim 15, wherein the antibody is a biological antibody.

17. The C-reactive protein microchip system of claim 11, wherein the body is in the form of flat-shaped.

18. The C-reactive protein microchip system of claim 11, wherein the potential change is caused by dynamic balancing relationship between potential energy of an equivalent circuit and a sensing circuit of the detector, and the potential change is related to an amount of the C-reactive proteins contained in the extracting solvent, wherein the equivalent circuit is formed with the sensing electrode and the extracting solvent in the second chamber.

19. The C-reactive protein microchip system of claim 11, wherein the detecting result is determined by a time coefficient of the potential change, and total detection time is less than 110 seconds.

20. A C-reactive protein microchip system comprising:
a body, comprising:
a first chamber including a C-reactive protein antibody imprinted polymer film having a plurality of imprinted nanocavities of claim 6 connected to a first portal and a second portal respectively, when a sample comprising C-reactive proteins is injected into the first chamber and flowing through the C-reactive protein antibody imprinted polymer film, flowing out of the first chamber from the second portal; and
a second chamber including a sensing electrode connected to a third portal and a fourth portal respectively, when an extracting solvent is injected into the first portal to extract the C-reactive proteins being captured by the imprinted nanocavities, flowing into the second chamber via the third portal, flowing out of the second chamber from the fourth portal; and
a detector, for detecting a potential change of the sensing electrode and generating a detecting result based on the detected potential change.

* * * * *